United States Patent
Hesse

(10) Patent No.: US 11,045,659 B2
(45) Date of Patent: Jun. 29, 2021

(54) METHOD AND DEVICE FOR THE IMPROVEMENT OF PHYSICAL FITNESS

(71) Applicant: Albert Hugo Hesse, Wenden (DE)

(72) Inventor: Albert Hugo Hesse, Wenden (DE)

( * ) Notice: Subject to any disclaimer, the term of this patent is extended or adjusted under 35 U.S.C. 154(b) by 0 days.

(21) Appl. No.: 16/120,352

(22) Filed: Sep. 3, 2018

(65) Prior Publication Data

US 2020/0069961 A1 Mar. 5, 2020

(51) Int. Cl.
*A61N 2/02* (2006.01)
*A61N 2/00* (2006.01)
*C12P 7/56* (2006.01)
*A61B 5/145* (2006.01)
*A63B 24/00* (2006.01)

(52) U.S. Cl.
CPC ............... *A61N 2/02* (2013.01); *A61N 2/004* (2013.01); *C12P 7/56* (2013.01); *A61B 5/14546* (2013.01); *A63B 24/0062* (2013.01); *A63B 2213/007* (2013.01)

(58) Field of Classification Search
CPC ......... A61F 5/0003; A61N 2/004; A61N 2/02; A61H 2201/10
USPC ....................................................... 600/9–15
See application file for complete search history.

(56) References Cited

U.S. PATENT DOCUMENTS

| | | | |
|---|---|---|---|
| 9,005,103 B2 | 4/2015 | Hesse | |
| 2004/0077921 A1 | 4/2004 | Becker et al. | |
| 2011/0105827 A1* | 5/2011 | Hesse | ............ A61F 5/0003 600/14 |

OTHER PUBLICATIONS

International Search Report and Written Opinion, dated Oct. 11, 2019, by the International Searching Authority in International Application No. PCT/EP2019/072587.
D. Abramson et al.: "Lactate Clearance and Survival Following Injury", The Journal of Trauma, vol. 35, No. 4, pp. 584-589 (1993).
S. Trzeciak: "Lac-time?", Crit Care Med, vol. 32, No. B, pp. 1785-1786 (2004).
M. P. Tarvainen et al.: "Kubios HRV—Heart rate variability analysis software", Computer Methods and Programs in Biomedicine, vol. 113, pp. 210-220 (2014).
C.-H. Hsu et al.: "Poincaréplot indexes of heart rate variability detect dynamic autonomic modulation during general anesthesia induction", Acta Anaesthesiologica Taiwanica, vol. 50, pp. 12-18 (2012).
D. Hoyer: "Zur Bedeutung und Analyse der Herzfrequenzvariabilität", Neurophysiologie-Labor, vol. 31, pp. 158-171 (2009), English Summary.
Z. Germán-Sallóet al.: "Non-Linear Methods in HRV Analysis", Procedia Technology, vol. 22, pp. 645-651 (2016).
D. S. Goldstein et al.: "Low-frequency power of heart rate variability is not a measure of cardiac sympathetic tone but may be a measure of modulation of cardiac autonomic outflows by baroreflexes", Exp Physiol, vol. 96, No. 12, pp. 1255-1261 (2011).
"Heart Rate Variability, Standards of Measurement, Physiological Interpretation, and Clinical Use", Task Force of the European Society of Cardiology the North American Society of Pacing Electrophysiology, Circulation, pp. 1043-1065 (1996).

(Continued)

*Primary Examiner* — Samuel G Gilbert
(74) *Attorney, Agent, or Firm* — Sughrue Mion, PLLC

(57) ABSTRACT

A method of lowering the blood lactate concentration of subject in the need thereof includes the step of applying to the subject a pulsating magnetic field to the thyroid area of the subject.

11 Claims, 12 Drawing Sheets

(56) References Cited

OTHER PUBLICATIONS

A. Bonen: "Lactate transporters (MCT proteins) in heart and skeletal muscles", Medicine & Science in Sports & Exercise, vol. 32, No. 4, pp. 778-789 (2000).

U. Boutellier: "Die Milchsäure", Schweizerische Zeitschrift für Sportmedizin und Sporttraumatologie, vol. 54, No. 3, p. 109 (2006), English Translation.

G.A. Brooks et al.: "Lactate as a Metabolic Signal of Gene Expression", Deutsche Zeitschrift für Sportmedizin, vol. 59, No. 12, pp. 280-286 (2008), English Summary.

C. Juel: "Lactate transport in skeletal muscle: Training-induced adaptation and significance in physical exercise", Deutsche Zeitschrift für Sportmedizin, vol. 55, No. 6, pp. 157-160 (2004), English Summary.

N. Maassen et al.: "Physiological 'Side-Effects' of Lactic Acid", Deutsche Zeitschrift für Sportmedizin, vol. 59, No. 12, pp. 292-296 (2008), English Summary.

H. Pilegaard et al.: "Effect of high-intensity exercise training on lactate/$H^+$ transport capacity in human skeletal muscle", the American Physiological Society, pp. E255-E261 (1999).

H. Stegmann et al.: "Lactate Kinetics and Individual Anaerobic Threshold", Int. J. Sports Medicine, vol. 2, pp. 160-165 (1981).

E. Wachter: "HRV-Schwellenbestimmung anhand Fahrradergometrie und Laufband im Verhältnis zu anaeroben Schwellen und Laktatschwellen", Refubium—Freie Universität Berlin Repository (2010), English Abstract.

J. Weineck: "Optimales Training Leistungsphysiologische Trainingslehre unter besonderer Berücksichtigung des Kinder- und Jugendtrainings", Spitta Verlag GmbH & Co. KG, No. 15 (2010), English Summary.

W. Wittling et al.: "Herzschlagvariabilität: Frühwarnsystem, Stress- und Fitnessindikator", Eichsfeld-Verlag, (2012), English Summary.

P. Wahl et al.: "Moderne Betrachtungsweisen des Laktats: Laktat ein überschätztes und zugleich unterschätztes Molekül, Schweizerische Zeitschrift für Sportmedizin und Sporttraumatologie", vol. 57, No. 3, pp. 100-107 (2009), English Abstract.

Y. Wang et al.: "$T_3$ increases lactate transport and the expression of MCT4, but not MCT1, in rat skeletal muscle", Am J Physiol Endocrinol Metab, vol. 285, pp. E622-E628 (2003).

H. Rohracher: Permanente rhythmische Mikrobewegungen des Warmblütter-Organismus ("Mikrovibration"), Die Naturwissenschaften, vol. 7/49 (1962), English Summary.

E. Gallasch et al.: "Characterisation of arm microvibration recorded on an accelerometer", Eur J Appl Physiol, vol. 75, pp. 226-232 (1997).

* cited by examiner

Nonlinear Results

| Variable | Units | Value |
|---|---|---|
| Poincare plot | | |
| SD1 | (ms) | 88.7 |
| SD2 | (ms) | 345.6 |
| Recurrence plot | | |
| Mean line length (Lmean) | (beats) | 30.70 |
| Max line length (Lmax) | (beats) | 817 |
| Recurrence rate (REC) | (%) | 48.01 |
| Determinism (DET) | (%) | 99.53 |
| Shannon Entropy (ShanEn) | | 4.195 |
| Other | | |
| Approximate entropy (ApEn) | | 1.047 |
| Sample entropy (SampEn) | | 0.888 |
| Detrended fluctuations (DFA): α1 | | 0.991 |
| Detrended fluctuations (DFA): α2 | | 1.037 |
| Correlation dimension (D2) | | 3.510 |
| Multiscale entropy (MSE) | | 0.888 – 1.200 |

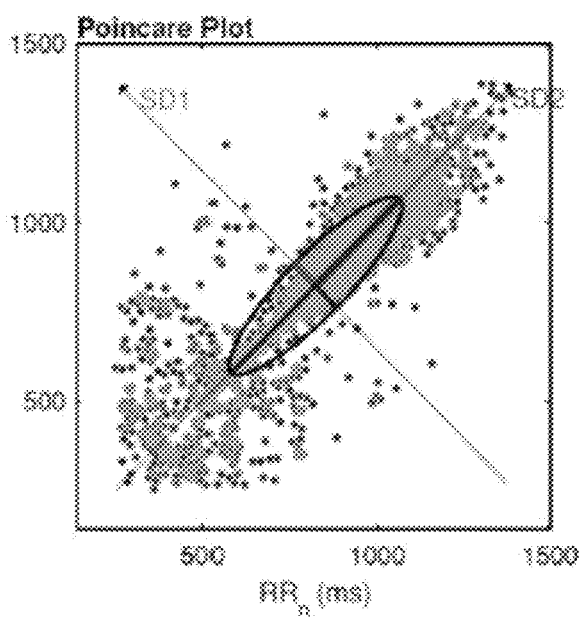 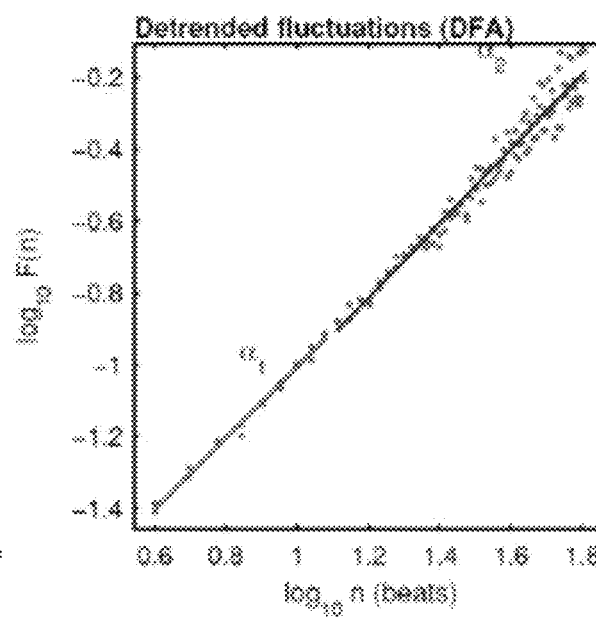

Fig. 5a

Nonlinear Results

| Variable | Units | Value |
|---|---|---|
| Poincare plot | | |
| SD1 | (ms) | 30.1 |
| SD2 | (ms) | 354.2 |
| Recurrence plot | | |
| Mean line length (Lmean) | (beats) | 58.66 |
| Max line length (Lmax) | (beats) | 988 |
| Recurrence rate (REC) | (%) | 50.79 |
| Determinism (DET) | (%) | 99.92 |
| Shannon Entropy (ShanEn) | | 4.803 |
| Other | | |
| Approximate entropy (ApEn) | | 0.559 |
| Sample entropy (SampEn) | | 0.305 |
| Detrended fluctuations (DFA):α1 | | 1.188 |
| Detrended fluctuations (DFA):α2 | | 1.278 |
| Correlation dimension (D2) | | 1.076 |
| Multiscale entropy (MSE) | | 0.298 – 0.510 |

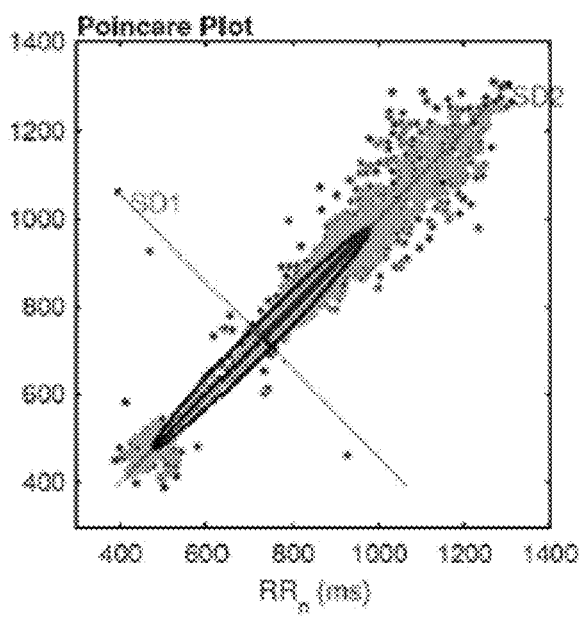
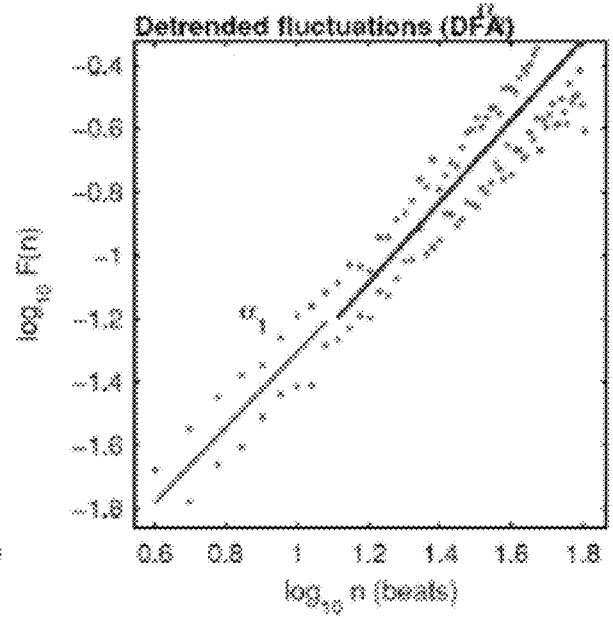

Fig. 6b

METHOD AND DEVICE FOR THE IMPROVEMENT OF PHYSICAL FITNESS

FIELD

The invention relates to the improvement and regeneration of physical fitness, especially after physical strain, and the enhancement of physical performance. More particularly, the invention relates to the field of lowering blood lactate values. Furthermore, it relates to a device and a method for the stimulation of the clearance of blood lactate and/or the reduction of the heart rate. In a further aspect the invention relates to a method for the treatment of hyperlactatemia and lactic acidosis.

BACKGROUND

High-intensity exercise training or any other physical strain contribute to the production and accumulation of blood lactate. Lactate is the end product of the anaerobic oxidative metabolism. It can be cleared by active recovery. However, there is no commonly agreed intensity or mode for optimal clearing of the accumulated blood lactate. Furthermore the natural recovery is often considered to slow. This in particular applies to athletes, who desire to regenerate fast and regain full physical fitness. They also desire a constant improvement of their physical performance.

Anaerobic metabolism occurs in athletic training or under any other high intensive physical strain when the energy requirement is greater than the energy supply. It usually occurs in the striated muscles. The energy is mainly produced by the cleavage of ATP (adenosine triphosphate). When ATP provides energy, a hydrogen ion (proton) is split off and remains in the muscle. This proton (H+) can lower the pH to critical values.

The pH value of the muscles is normally neutral (pH of approximately 7). If the value falls below pH of 7, such a pH value can lead to cell damage. For this reason, the body has developed a defense mechanism. To bind the protons, the body produces more lactate, which can bind protons. Thereby the over-acidification of the muscle is counteracted. This protective mechanism eventually reaches its limits. If the pH value in the muscle cell continues to decrease while the number of protons continues to increase, the protons finally block the ATP cleavage and the muscle tenses (the muscle "closes").

The lactate thus ensures that a highly intensive strain can be continued for a certain period of time before the muscle cramps. The more lactate in the blood, the higher the number of protons in the muscle, and the higher the strain on the body. Based on the lactate in the blood, the degree of stress can be determined and the body's ability to maintain intensive stress for a certain period of time.

The lactate level in the blood can be determined as a result of the continuous formation and degradation of the lactate. In healthy humans at rest the blood lactate concentration is maintained within the range of 0.5-1.5 mmol/l.

Lactate steady state is of great importance for athletes, sports medical examinations or the individual performance measurement and control. For example, in the usual endurance tests (e.g. on a bicycle ergometer), the physical strain on the patient/proband is gradually increased after a certain period of time. In the case of the bicycle ergometer, this load can be regulated via the resistance. The lactate level in the blood then rises measurably because the muscles need more energy to perform better. This means that a relatively large amount of lactate can be determined for a short time. After some time, a balance (=new steady state) will level off again for exactly this load level. The lactate levels in the subject's blood would not change now. This principle is followed until there is no more steady state, because the body can no longer compensate for the now considerably increased load. This results in a continuous increase in lactate, which ultimately also determines the state of exhaustion and allows the test subject to complete the test.

The lactate concentration in the blood is measured. This can be invasive, e.g. at the earlobe. Alternatively non-invasive methods can be used. At low or moderate physical activities the lactate value of a healthy adult human is approximately 2 mmol/l. This is called the aerobic threshold. In this phase the resulting lactate is sufficiently eliminated by the body. If the value of the lactate production corresponds to the value of lactate elimination, this is called the lactate steady-state (at 2-4 mmol/l). The anaerobic threshold is approximately 4 mmol/l. Top athletes can have lactate values of up to 25 mmol/l.

Simple measures hardly affect the lactate value. For example, the diet has almost no lowering effect on the lactate level in the blood. Although a thiamine deficiency (vitamin B1) can increase the lactate level in the blood, the inverse conclusion that vitamin B1 has a significant lactate degrading effect does not hold true.

SUMMARY

It is therefore the objective of the invention to provide a method for the reduction of blood lactate levels in mammals, in particular in humans and, furthermore, a method for the stimulation of blood lactate clearance. This method should serve to enhance the regeneration of the subject after physical strain and/or to improve his physical fitness (performance).

This objective is solved by a method of treating a subject in the need thereof, in particular a subject with a blood lactate level of at least 1.5 mmol/l, by applying to the subject a pulsating magnetic field to the thyroid area of the subject. The magnetic field preferably has a field strength in the range from 0.1 to 100 µT. The frequency is, in a preferred embodiment, a single frequency selected from the range of 1 to 100 Hz.

BRIEF DESCRIPTION OF THE DRAWINGS

The present invention is described in greater detail below on the basis of embodiments and of the drawings in which:

FIG. 5a shows the HRV data of the control, a baseline measurement without intervention of the Thyreogym;

FIG. 6b shows the same assessment as FIG. 5a under the treatment with Thyroegym.

DETAILED DESCRIPTION

Figure 1A:
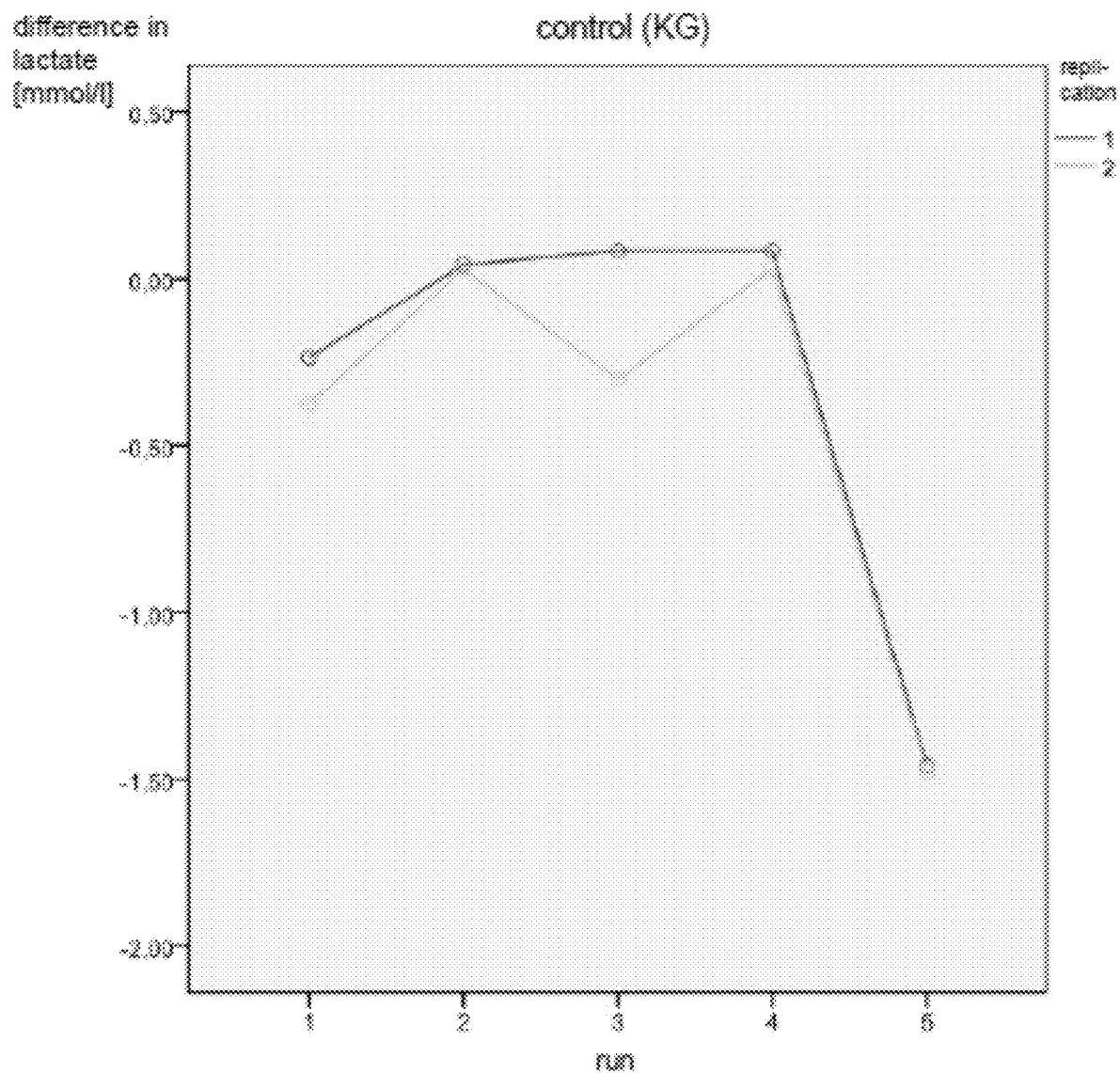
FIG. 1a shows, for the lactate values, the difference within 10 minutes was examined during the break times, as well as their heart rate value within the documented period between all stress phases (5 runs; two replications)

The inventor has found that with the treatment according to the invention the blood lactate level of the treated subject can be reduced. This can either be due to the fact that the clearance of the lactate in the blood is stimulated (enhanced), i.e. compared to a non-treated subject the lactate concentration in the blood decreases faster. However, this can also be due to a decrease formation of lactate during or before physical strain. Both effects can contribute to a lower level of lactate in the blood.

By applying the method of the invention as exemplified below (cf. the examples below) the inventor observed in the subjects of the treatment group a reduction of the blood lactate value by 0.8 to 1.4 mmol/l determined after the treatment of the subjects in the intervals between two periods of physical strain.

The inventor also found that due to the treatment of the invention the heart rate of the subjects was substantially reduced. Compared to the control group the heart rate was lowered by 8 to 10 beats per min (cf. examples below). Hence the method of the invention can also be applied for the reduction of the heart rate of the subject in the need thereof. It furthermore impacts on the heart rate variability of the subject. The heart rate variability is indicative for the stress releasing properties of the treatment and the improvement of physical recovery. Accordingly, the method of the invention also relates to a method for the amelioration of the physical constitution in a subject after physical strain which comprises applying a pulsating magnetic field as outlined above.

The method of the invention applies to all mammals. In particular it can be used for the treatment of human subjects. In a preferred embodiment the human subject is an athlete. Most preferably the subject is an adult, i.e. a human in the age of at least 16 years.

The subject can be treated by either applying the pulsating magnetic field before a physical strain or after the physical strain, advantageously directly after the termination of the physical strain. In order to be most effective the treatment can be applied to the subject at rest as well as directly after the physical strain has terminated. The application at rest preferably is a long term treatment, in particular a once daily application for at least one week, more preferably at least for two weeks, more preferably for at least three weeks. The application in this long term treatment preferably is for a duration of 1 to 60 min.

The term "physical strain", with respect to adult humans, is defined as a physical activity that requires a performance of the subject of at least 50 Watt. Consequently a subject (in particular an adult human) is "at rest" if the subject performs an activity of below 50 Watt. This is a typical level of easy working.

In a preferred embodiment of the invention the method applies to physical strains of more than 75 Watt (this performance typically is required with light or moderate bicycling), even more preferred of more than 100 Watt (this is typical for bicycling with moderate to vigorous efforts). Most preferred is the application of the method to adult humans who perform or intend to perform physical activities (strains) of more than 150 Watt. This level is typical for activities such as running.

Hence the method of treatment according to the invention can be used to strengthen the physical fitness of a subject, and thereby improve its physical performance. Furthermore it can be used to accelerate the physical recovery of a subject after physical strain, in particular of physical strains of more than 100 Watt, even more preferred to physical strains of more than 150 Watt. It can also suitable for the treatment of soreness. Thus, in yet another aspect of the invention the treatment is applied to treat or to prevent soreness or any other overload of muscles during physical strain.

For athletes it is particularly interesting that the method of the invention can be applied to shift the individual anaerobic threshold. With "shifting the anaerobic threshold" it is meant that the physical performance of the subject is improved before reaching the anaerobic threshold. The invention thus particularly applies to a method for improving the physical performance of a subject, in particular of an adult human.

In yet another aspect of the invention the method can be applied to treat hyperlactatemia or lactic acidosis in a subject in the need thereof, in particular a human. Hyperlactatemia is a pathological state in which resting blood lactate concentration is abnormally high (>1.5 mmol/L). Moderate to severe hyperlactatemia (>3.0 to >5.0 mmol/L) is associated with abnormal accumulation of hydrogen ions (H+) and a resulting tendency to acidosis. In the presence of oxygen, hydrogen ions produced during ATP hydrolysis are utilized in the mitochondrial process of oxidative phosphorylation, but this is often not possible in the context of anaerobic glycolysis associated with lactate production (cf. outlined above). Instead, hydrogen ions accumulate in blood, eventually overwhelming the bicarbonate and other buffering systems that maintain blood pH within normal limits (7.35-7.45).

The combination of hyperlactatemia and acidosis is called lactic acidosis. It is defined in the context of the present invention when the blood lactate >5.0 mmol/L in combination with pH<7.35. Lactic acidosis is the most common cause of metabolic acidosis.

Mild to moderate hyperlactatemia (blood lactate <5 mmol/L) causes no specific signs and symptoms. As lactate levels rise above 5 mmol/L, there is an increasing risk of the clinical manifestations of lactic acidosis, which are tachycardia (increased heart rate) tachypnea (increased respiratory rate) and alteration in mental status that can range from mild confusion to coma. The deep sighing respiration (Kussmaul's respiration), a compensatory response to any form of metabolic acidosis, may be evident.

Blood lactate measurement has a value also in the emergency room and intensive care unit because, irrespective of the mechanism of hyperlactatemia, blood lactate concentration predicts morbidity and mortality. The prognostic value of lactate measurement has been confirmed in many patient groups. For example, in a prospective study of 76 major trauma victims serial lactate measurements were made over the first 48 hours after admission (Abramson D, Scalea T M et al. Lactate clearance and survival following injury. J Trauma 1993; 35: 584-88). All 27 patients whose lactate normalized within 24 hours survived but only three of 22 patients whose lactate remained raised at 48 hours survived.

These and many other studies have demonstrated that raised lactate in the context of trauma, sepsis and critical illness generally is a prognostic sign indicating the need for immediate and intensive resuscitative measures. If these are effective in reducing blood lactate within 24-48 hours, the chances of survival can be greatly increased (Trzeciak S. Lac-time? Crit Care Med 2004; 32: 1785-86).

From this it follows that the method according to the invention can also be applied, as outlined above, to treat in a subject in the need thereof hyperlactatemia or lactic acidosis.

As above, the magnetic field can have a field strength (flow density) in the range of 0.1 to 100 µT. In a preferred embodiment the field strength ranges from 20 to 80 µT, even more preferred it ranges from 45 to 55 µT. Most preferred the field strength is 50 µT.

The single frequency of the magnetic field can preferably be selected from the range of 1 to 100 Hz, more preferably from the range of 3 to 60 Hz, even more preferred from the range of 7 to 20 Hz. The most preferred single frequency is 14 Hz. It is possible, in accordance with the present invention, to adjust the frequency of the pulsating magnetic field to a Schumann-resonance frequency.

In one embodiment of the present invention, the impulse form of the magnetic field is illustrated by a simple wave function, especially preferred as a sinus curve, as a rectangular curve, a trapezoidal curve or a saw tooth curve. Optionally, the impulse form, that is the pulsation of the magnetic field, is temporally changeable, that is, during the period of application the magnetic field can be changing.

The period of applying the method of the present invention, or the duration of the treatment with the device according to the present invention can be determined individually and can extend for a period of days up to weeks and months. A continuous treatment is also possible, which will, as the case may be, interrupted only by periods of sleeping. A daytime application can be varied likewise in individual manner, and can be one time or several times a day. An application cycle can last, for example, from several minutes to several hours. The device can comprise a control unit which allows individual programming for an individualized application plan.

In a most preferred embodiment the method of the invention is applied to the subject at rest daily at least once, at least for 5 min, more preferred at least for 10 min. Preferably it is applied for a period of 1 to 60 min, 10 to 40 min, most preferred for 30 min.

Alternatively or—in one even more preferred embodiment—additionally, the method is applied directly after the termination of the period of physical strain. If the subject is an athlete, it can be applied directly before and/or after a training or competition. The duration of applying the method after strain advantageously can be at least 3 min, at least 5 min and most preferred at least 10 min.

The method according to the present invention can be supported with the intake of food supplements. Preferred are polyphenol-rich polyphenol and aromatic compounds with two or more hydroxyl groups that are directly bound to the aromatic ring such as attributed to secondary plant stuffs. Polyphenols are contained in plants, which are rich in antioxidants and thus support health. Examples of polyphenol rich foods are apple berries, red grapes, red wine, mangosteen (*Gracinia mangostana*), pomegranates (*Punica granatum*), gingko, tea in particular, green tea, zistroses, the seeds of perills (*Perila frutescens*), Chinese lemon balm or turmeric. Within the scope of the present invention, polyphenol is defined as isolated or chemically synthesized polyphenol. Examples of isolated polyphenols are quercetin or resveratrol. The device according to the present invention and its application are thus suitable for a combination with the above identified agents.

According to another aspect of the present invention, a device is provided for the application of a pulsating magnetic field to the subject in the need thereof, in particular to a human subject, most preferred to the thyroid of the subject. Such a device, in general, is known from U.S. Pat. No. 9,005,103 B2, which describes the effect of a pulsating magnetic field on the free T3 and free T4 blood levels. Such a device includes a generator module for the generation of a magnetic field and a control unit that can be attached closely to the body of a mammal or a volunteer. The generator module produces a pulsating magnetic field preferably of a frequency of from 3 to 60 Hz, preferably a frequency of 7 to 20 Hz, especially preferred of a frequency of 14 Hz.

As outlined above, the magnetic field applied according to the invention is a pulsating magnetic field. The control of the pulsation is preferably electronic and not mechanical, for example, by using a switching circuit. As compared to a mechanical control, which could be for example, a rotating permamagnet, the electronic control has the advantage of a much lower noise level and a reduced energy use which leads to a longer life expectancy of the device.

Preferably, the device is free of permamagnets, such that in the "off" mode of the device, no magnetic field is being generated and thus any undesired effects avoided. It is further preferred that the device, aside from any impact resulting from the attachment of the device to the body, no other mechanical stresses accompany the attachment of the device to the surface of the body, in particular, the attachment to the thyroid, and to so prevent irritations due to mechanical forces.

The module that generates the magnetic field according to the present invention is housed in the device, which is preferably designed for close attachment to the body of the volunteer, so that activation of the thyroid can be carried out in optimal manner. The scope of the activation or the amount of the activation is adjustable via the size of the module, the length of application, the force of the magnetic field and/or the properties of the magnetic field.

The device according to the present invention can be applied in nearly all life situations, for example during a work related activity, while resting or during sports activities, at home or when traveling. This becomes essential especially for long term application.

The device has the advantage that it can be utilized and applied by persons not having special technical background. Thus, the user can attach the device to his body without assistance from medically trained personnel and can activate the generator module. The device according to the present invention permits a simple application.

The device according to the present invention can be configured for close to the body wearing, that is, either wearing it directly at the body of the volunteer (human or animal) or at or in the clothing or equipment (harness i.e. halter) which are worn at the body. The generator module generating the magnetic field should preferably be disposed in the device for positioning at or directed at the thyroid or also the neck of the volunteer during the application of the device.

The generator module can be adjusted to the size or shape of the thyroid. Thus, the generator module, for example, can be fashioned in the shape of a butterfly. In a preferred embodiment, the maximum size of the body surface of the neck is maximally 200 cm$^2$, preferably maximally 150 cm$^2$, especially preferred maximally 100 cm$^2$ or maximally 50 cm$^2$.

In one embodiment, the device is configured as a flat support, for example as a neck band, neckerchief, scarf, shawl or a neck brace or neck support. In this manner, a possibly largest contact surface between the neck region of the volunteer and the generator module of the device is realized. The module can be supported by the support or it can be integrated into the support. Likewise, an attachment can be onto or can be integrated into equipment such as clothing, for example jackets, coats or vests.

The device can also be directly attached to the skin. In this case, the support can be configured as a patch.

The device can also be integrated into accessories, or it can form an accessory, for example a piece of jewelry, a head band, a collar, and a veil or similar.

The attachment of the device at the body can be realized in any known ways. Accordingly, the configuration of the device can include attachment elements, for example, rivets, buttons, toggles, bands, buckles, hooks, zippers or hook and loop closures.

The device according to the present invention can be constructed as a textile product, for example, as a woven or knitted fabric, as a felt or milled fabric, or non-woven web or formed fabric. Advantageously, these textiles are flexible and thus may optimally and individually adapt to the body area to be treated. When the device is constructed in a flat shaped embodiment, it improves the wearing comfort and adjustment of the volunteer with the positive effect that it will enhance the therapy compliance of the volunteer.

In one embodiment, the device itself can be a piece of clothing or at least a portion thereof. The piece of clothing can have corresponding adjustment elements such as a hook and loop closure or a strip of buttons or similar, by which the device can be individually adjusted to each volunteer.

The single constituents of the device can be chosen as light weight as possible with a view toward the utmost comfort for the volunteer.

The electronic constituents of the device, such as for example, the generator module, cables or electronic control can be attached at the device and need not represent separate parts of the device, that is, they are integrated into the device and not detachable without destroying the device. Any one or more of the electronic constituents can be integrated into the device in this manner.

It is also possible to configure the device so that the electronic constituents are detachable from the device without causing its destruction. This would be advantageous for exchanging single constituents or replace them for repair.

The electronic constituents of the device can be either in whole or in part applied at the volunteers clothing or accessories. In an advantageous embodiment, the components can be applied in an invisible manner so they cannot be spotted by others, for example in the inner lining or inner pocket of a jacket, in a muffler or scarf, or in the knot of a tie or a bow tie, or the part can be itself in the form of an accessory.

The device can send out acoustical, optical or tactile signals including vibration signals that indicate certain functional conditions, for example, indicating the state of charge, indicating an interference or signaling the end of the treatment period. It can also serve to remind the user of certain action to be taken, such as for example, to attach the device or to remove the device.

To supply the device with energy, batteries can be utilized, preferably of the size A, AA or button batteries, also those batteries that can be recharged. Alternatively, other current producing devices, such as solar cells or miniature wind generators can be utilized. The generator module, as aforestated emits a pulsating magnetic field.

The device according to the present invention is especially preferred when comprising a generator module for generating a magnetic field and a control unit and is attachable close to the body of the mammal and wherein the generator module is capable of producing a pulsating magnetic field with a frequency in the range from 1 Hz to 100 Hz, preferably 7 Hz to 20 Hz and especially preferred with a frequency of 14 Hz.

The flow density of the magnetic field can be in the range of 0.1 to 100 µT. Optionally, the flow density is time dependent, for example, by an exponential increase and/or decrease.

The device according to the present invention is controllable relative to the properties of the magnetic pulsation with respect to strength, frequency and/or form of pulsation and is adjustable to the duration of treatment, frequency and duration of a single application to concrete, individual therapeutic requirements. In a suitable embodiment, these properties can likewise be individualized via the control unit and programmed in corresponding manner.

In an especially preferred embodiment of the present invention, the device is configured as a neck band which includes an actuating generator module for generating a magnetic field, an electronic control and an exchangeable energy supply. It is preferred to utilize one or more coils for the generator module.

"Neck band" within the scope of the present invention is a flat support in band or string shape for placing around the neck.

The term "generator module" is any device which is capable of generating a static or pulsating magnetic field. A static magnetic field can be generated by one or more permamagnets or an electric magnet without a pulsating flow of current. Advantageously, a pulsating magnetic field includes a generator module of one or more coils of current conducting material such as for example, copper wire.

The term "pulsating magnetic field" within the scope of the present invention, is generally a magnetic field that changes over time and whose intensity during the passage of time includes more than one local maximum. For example, exponentially increasing and/or exponentially decreasing pulses are possible. The pulsating magnetic field is preferably one that is characterized by periodically varying magnetic fields also known as magnetic pulsations, by frequency, impulse form and strength.

The invention will be described below with detailed examples. The examples are for illustrative purposes only. Nothing in the examples is meant to limit the scope of the invention.

Embodiments of the Invention

1. A method of lowering the blood lactate concentration of subject in the need thereof by applying to the subject a pulsating magnetic field to the thyroid area of the subject.
2. The method according to embodiment 1 for the recovery of the subject after physical strain.
3. The method according to embodiment 1 for the increase of physical fitness.

4. The method according to embodiment 1 for the shift of the individual anaerobic threshold.
5. The method according to any of the embodiments 1 to 4, whereas the magnetic field has a field strength in the range from 0.1 to 100 µT, in particular from 20 to 80 µT, more preferred from 45 to 55 µT, most preferred a field strength of 50 µT.
6. The method of any embodiment 1 or 5, whereas the pulsating magnetic field as a single frequency selected from the range from 1 to 100 Hz, in particular from 30 to 60 Hz, more preferred from 7 to 20 Hz, most preferred of 14 Hz.
7. The method of any embodiment 1 or 5, whereas the pulsating magnetic field has a field strength of 50 µT and a single frequency of 14 Hz.
8. The method according to any of the above embodiments, whereas the subject has a blood lactate level of at least 1.5 mmol/l.
9. The method according to any of the above embodiments, wherein the pulsating magnetic field is applied at least once daily.
10. The method according to any of the above embodiments, wherein the pulsating magnetic field is applied to the subject at rest.
11. The method according to any of the above embodiments, wherein the pulsating magnetic field is applied for a duration of 1 to 60 min.
12. The method according to any of the above embodiments, wherein the pulsating magnetic field is applied directly after the termination of physical strain, in particular for a duration of at least 3 min, preferably of at least 5 min, most preferably of at least 10 min.
13. The method according to any of the above embodiments, wherein the pulsating magnetic is applied in the interval between two physical strains.
14. The method according to any of the above embodiments, wherein the physical strain is of at least 75 Watt, more preferred of at least 100 Watt, most preferred of at least 150 Watt.
15. The method according to any of the above embodiments, wherein the subject is an adult human.
16. The method according to embodiment 1 for the treatment of hyperlactatemia or lactic acidosis.
17. The method of any of the embodiments 1 to 16, wherein the form of the pulsating magnetic field is selected from the group consisting of a sinusoid, a rectangular curve, a trapezoidal curve and saw tooth curve.

EXAMPLES

1. Background and Structure of the Study

The objective of the study was the question whether a non-invasive stimulation of the thyroid gland can increase physical performance in adult humans. For this purpose, in particular two physiological parameters (heart rate and lactate value) were determined from healthy subjects. A device was used to stimulate the thyroid gland; namely the device "Thyreogym" of Thyreogym GmbH, Lennestadt (Germany). The magnetic field of the Thyreogym has a field strength of 50 µT and a single frequency of 14 Hz.

37 subjects aged 16 to 42 (men and women) took part in the study. These probands were mainly athletes from the fields of triathlon, athletics, hockey, soccer and handball. Test persons with thyroid hyperfunction or hypofunction, infectious diseases, diseases of the immune system or neurological diseases were excluded.

2. Treatment

The probands of the treatment group used the Thyreogym at rest once daily for 30 min for a period of three weeks. Furthermore they applied the Thyreogym for 10 min after a physical strain. The physical strain was at least 50 Watt.

The physical strain on the test persons took place in two runs in which the load was increased in steps according to the Mader model (increase by 2 km/h at a distance of 500 meters, with an initial speed of 8 km/h; increase then to 10 km/h, 12 km/h, 14 km/h and 16 km/h).

The heart rate and the lactate value of all probands were determined at baseline, i.e. before the first use of the Thyreogym.

3. Evaluation of Lactate Values and Heart Rate

Lactate values were determined using the Lactate Scout system with the EKF Diagnostics. Heart rate data was collected using Kubios HRV Premium 3.0.2 and Garmin Express Forerunner 920XT. These devices were used according to the standard instructions of the manufacturers. The evaluation was done via the Software easy Lact 1.2, LSA V1.06.

4. Results

The results of the study show a positive effect of non-invasive stimulation of the thyroid gland on the physical performance and regenerative capacity of the probands. With the treatment the heart rate of the subject could be reduced by 8 to 10 beats on average. Compared to the control group the lactate blood values after physical strain were reduced by an average of 0.8 to 1.4 mmol/l.

The subjective feelings of the test persons could also be improved. Some of the probands reported less muscle pain or hardening and an overall better feeling of movement. The regeneration phases between the stress phases could also be shortened. Performance losses due to previous physical overloads were reduced.

Stimulation of Lactate Degradation

Between the runs the lactate values and the heart rate data of the test persons were collected. For statistical evaluation, PASW Statistics Base 18 Version 18.0.0 (Polar Engineering and Consulting, USA) was used to perform a descriptive analysis of the explorative data of the regeneration phases during the breaks between the runs.

Figure 1B:
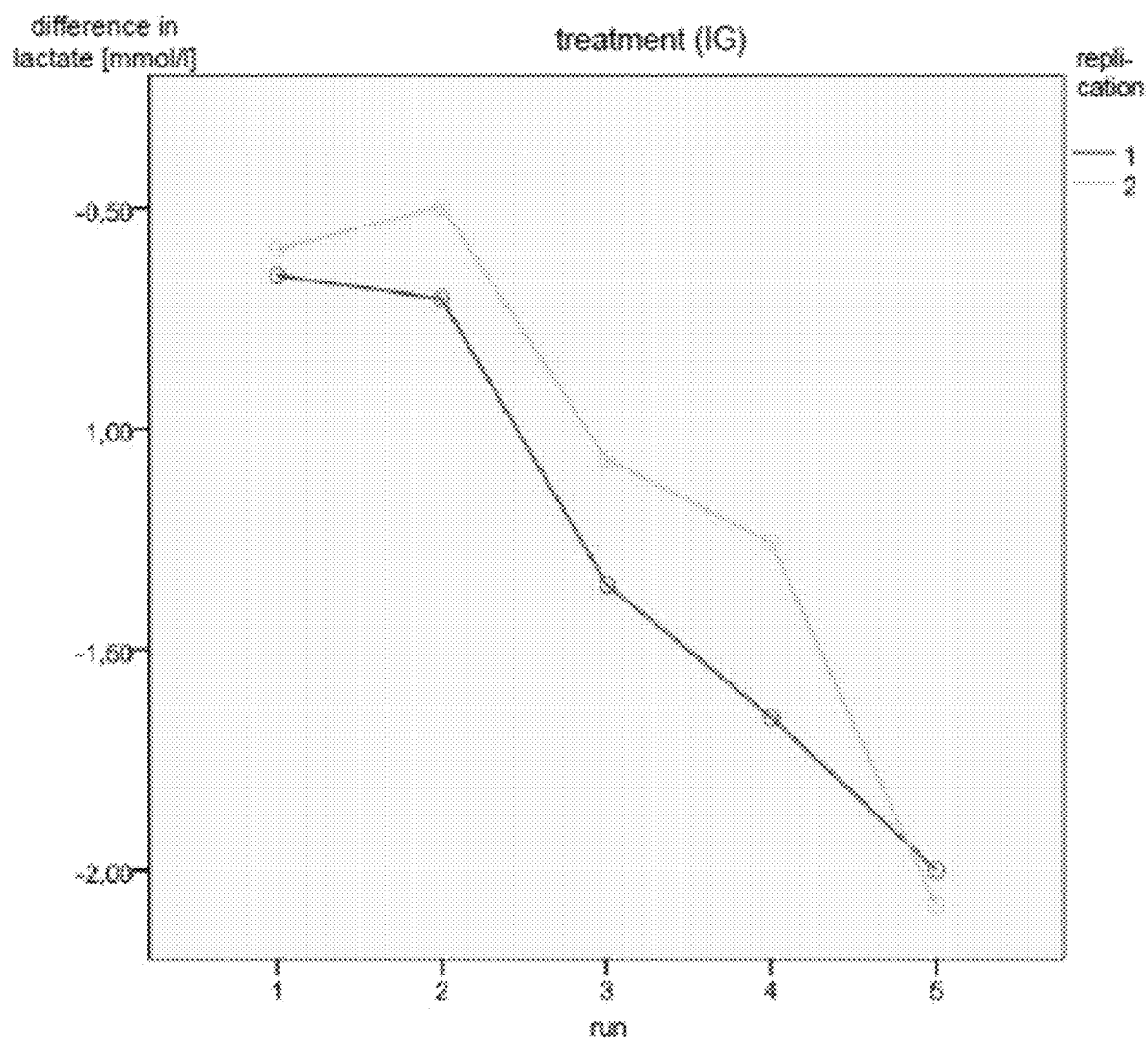
FIG. 1b shows, for the lactate values, the difference within 10 minutes was examined during the break times, as well as their heart rate value within the documented period between all stress phases (5 runs; two replications)

For the lactate values, the difference within 10 minutes was examined during the break times, as well as their heart rate value within the documented period between all stress phases (5 runs; two replications; FIGS. 1a and 1b).

All data have been tested with mean±standard deviation (SD) and corresponding reference ranges with a confidence interval, unless otherwise noted. The Mauchly test for sphericity and the Greenhouse-Geisser test were used to test for normal distribution of group analyses.

Two repetitions were performed. The X-axis shows the runs (8 km/h, 10 km/h, 12 km/h, 14 km/h and 16 km/h, denominated as "run" 1, 2, 3, 4 and 5). The Y-axis lists the respective decrease (difference) of the lactate values in the pause immediately following the run. After the fifth run, the average reduction in lactate levels is highest in the treatment group.

It turned out that after each further run the reduction of the lactate value increased (i.e. the stimulation of the lactate decomposition by the treatment increased. In the treatment group the mean difference (indicating the lactate clearance) continuously increased from run 1 to run 5. In contrast, the difference in the control group initially remains almost constant over the runs 1 to 4. This shows that the lactate degradation was accelerated by the treatment.

Figure 2A:
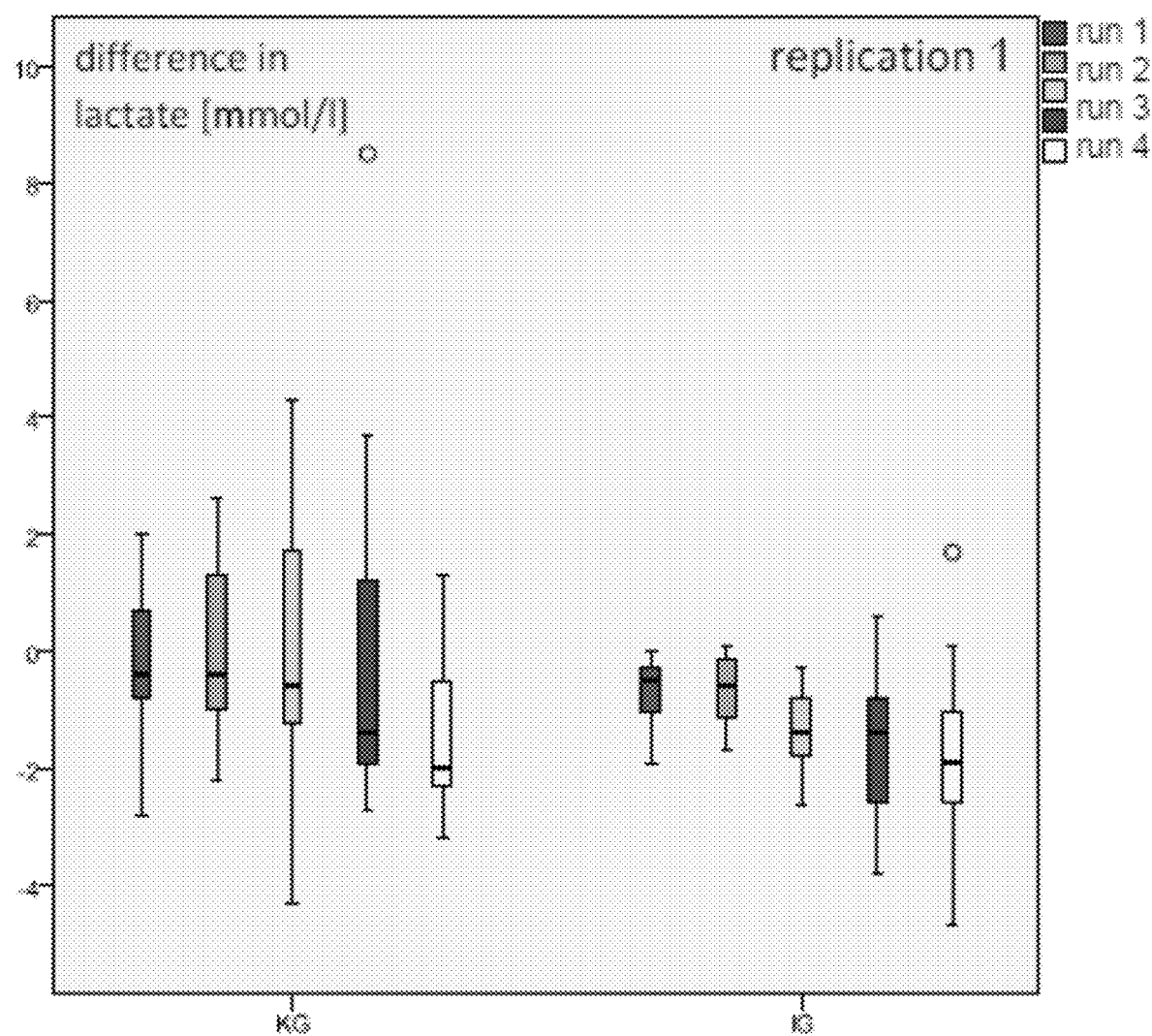
FIG. 2a shows the effect of the treatment in a box plot.
Figure 2B:
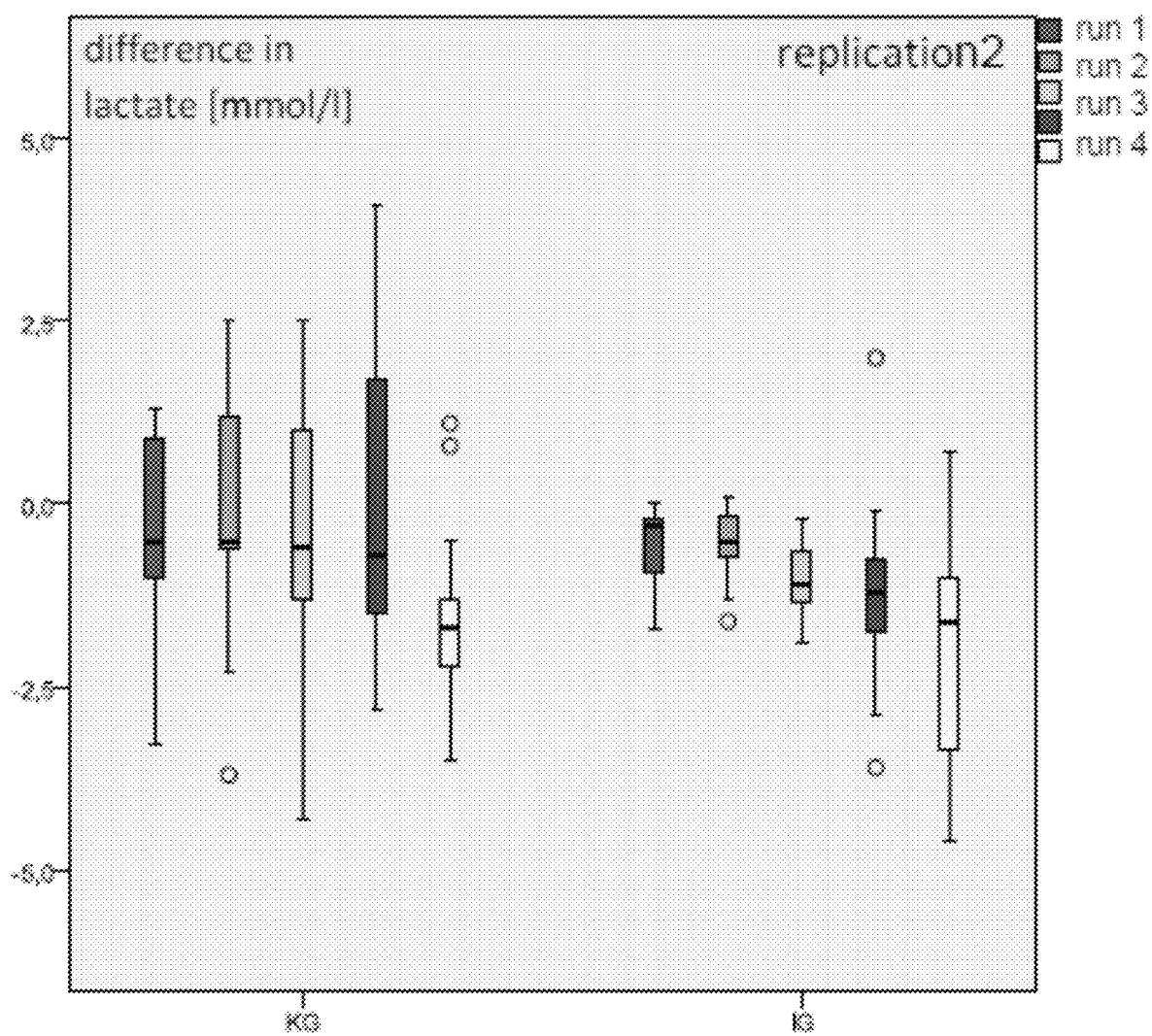
FIG. 2b shows the effect of the treatment in a box plot.

The effect of the treatment can also be seen in the box plots (FIGS. 2a and 2b).

Reduction of Lactate Formation

The data also show that using the Thyreogym reduced the formation of lactate. This can be concluded from the absolute values of the lactate measurements. This values refers back to the lactate value at baseline, i.e. the lactate value before the use of Thyreogym. A difference of above −0.5 mmol/l after the first run in the control group compared to a difference of below −0.5 mmol/l in the treatment group indicates that the lactate value of the treatment group initially had been lower. This is due to the use of Thyreogym also at rest.

Reduction of Heart Rate

Figure 3:
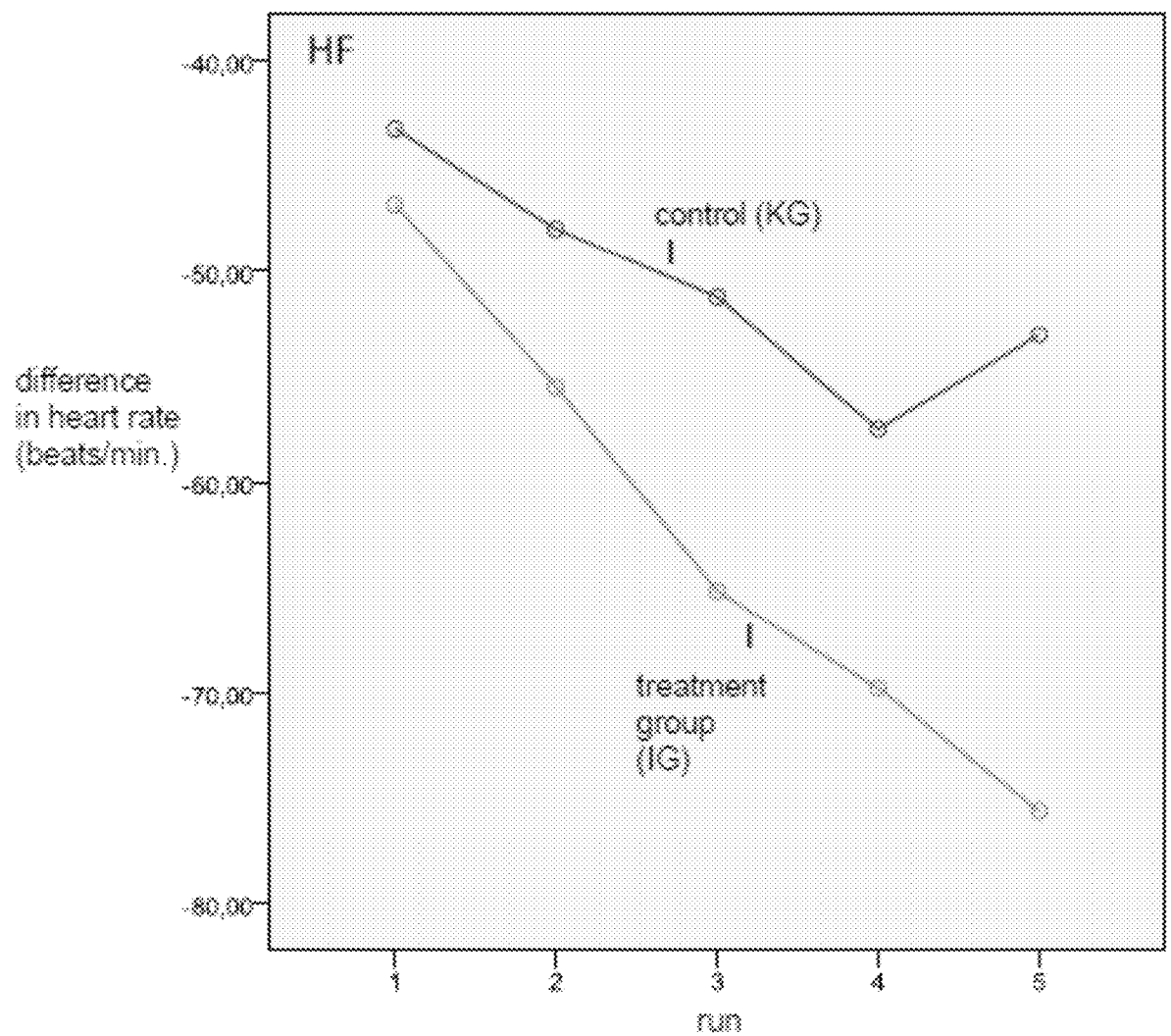
FIG. 3 shows a comparison of the development of the heart rate in the treatment group versus the control group.

The average heart rate reduction in the treatment group decreased due to the treatment. In the control group also a reduction could be observed, but less pronounced. FIG. 3 shows a comparison of the development of the heart rate in the treatment group versus the control group.

For the assessment of the heart rate reduction the difference between the maximum heart rate during a run and the heart rate 10 min immediately after the termination of the previous run was determined. This heart rate difference indicates the regeneration of the proband before the next run.

Figure 4:
FIG. 4 shows an example of a proband's heart rate during two runs.

The effect of the treatment on the heart rate is also shown in FIG. 4. FIG. 4 shows an example of a proband's heart rate during two runs. In the second run (lower curve) the proband applied the Thyreogym during the breaks between the intervals of running. These data indicate that the heart rate is significantly lowered due to the treatment of the invention. The reduction in heart rate reflects the subject's ability to regenerate after intensive physical exercise.

Exemplary Performance Curves (Case Studies)

Heart Rate Variability (HRV)

The impact of the treatment on the heart rate variability is shown by the comparison of FIGS. 5 and 6.

Figure 5B:
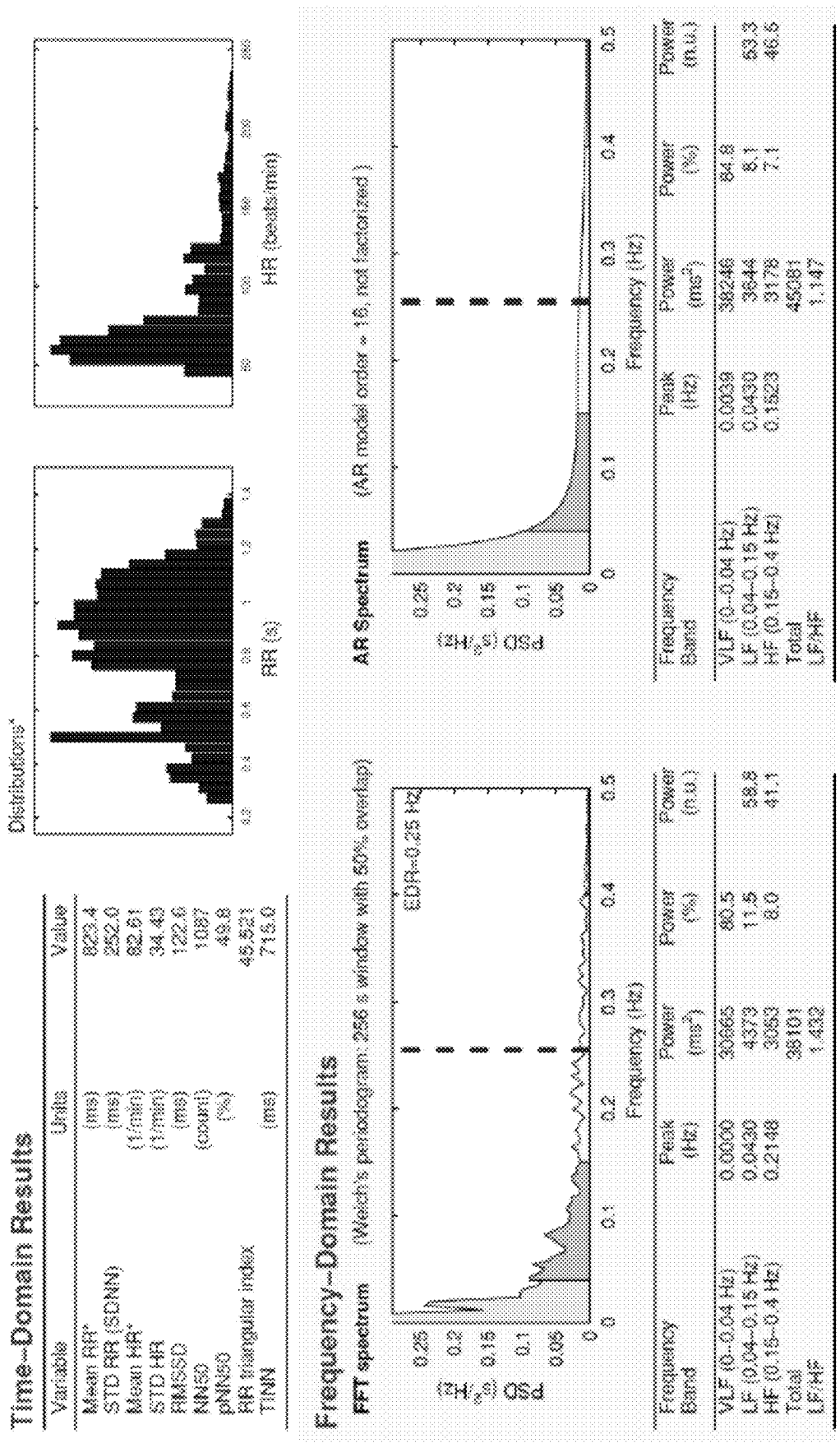
FIG. 5b shows the HRV data of the control, a baseline measurement without intervention of the Thyreogym.
Figure 6A:
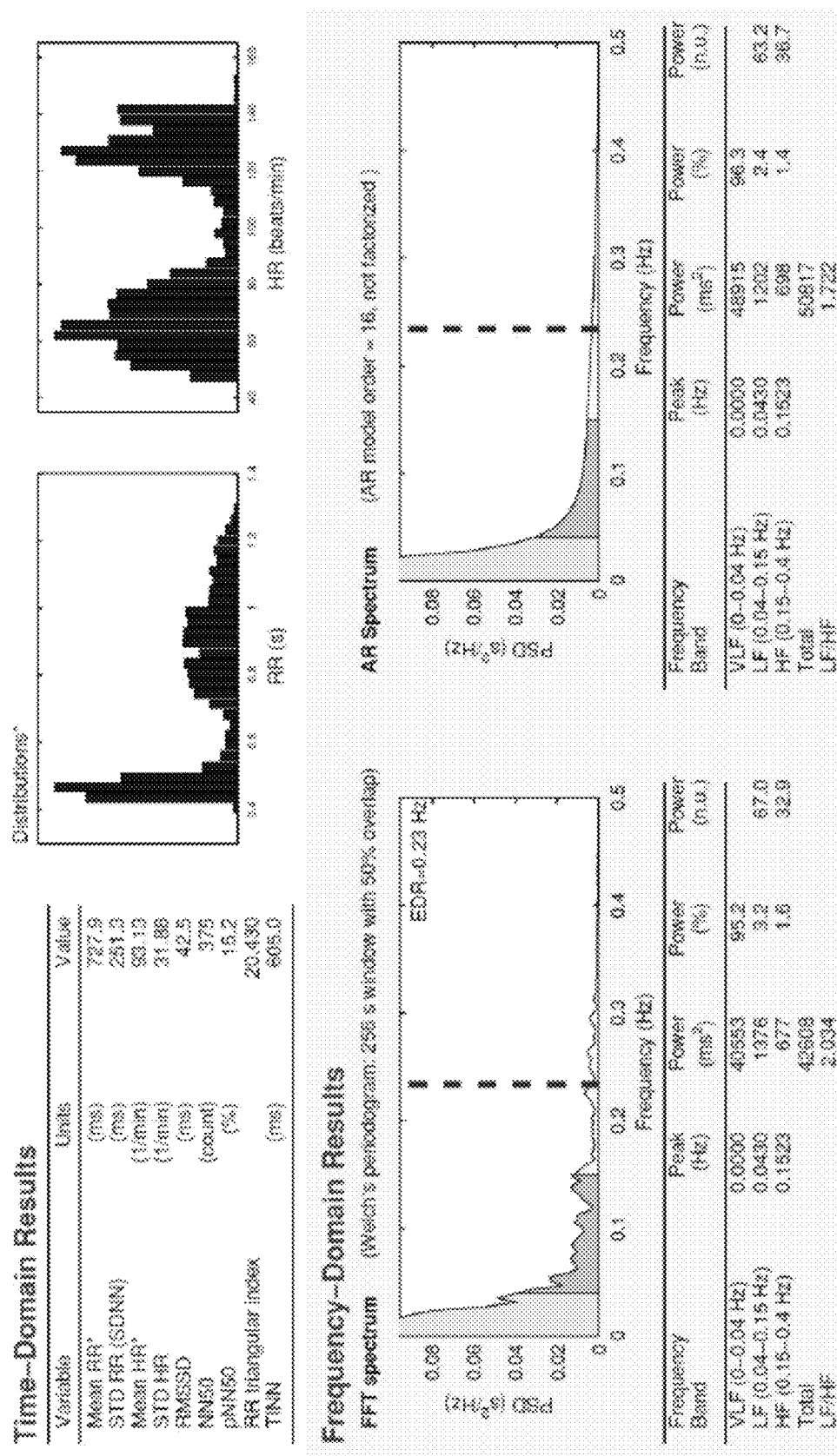
FIG. 6a shows the same assessment as FIG. 5b under the treatment with Thyreogym.

FIGS. 5 and 5b and 5b show the HRV data of the control, a baseline measurement without intervention of the Thyreogym. FIGS. 6a and 6b show the same assessment under the treatment with Thyreogym.

Figure 7:
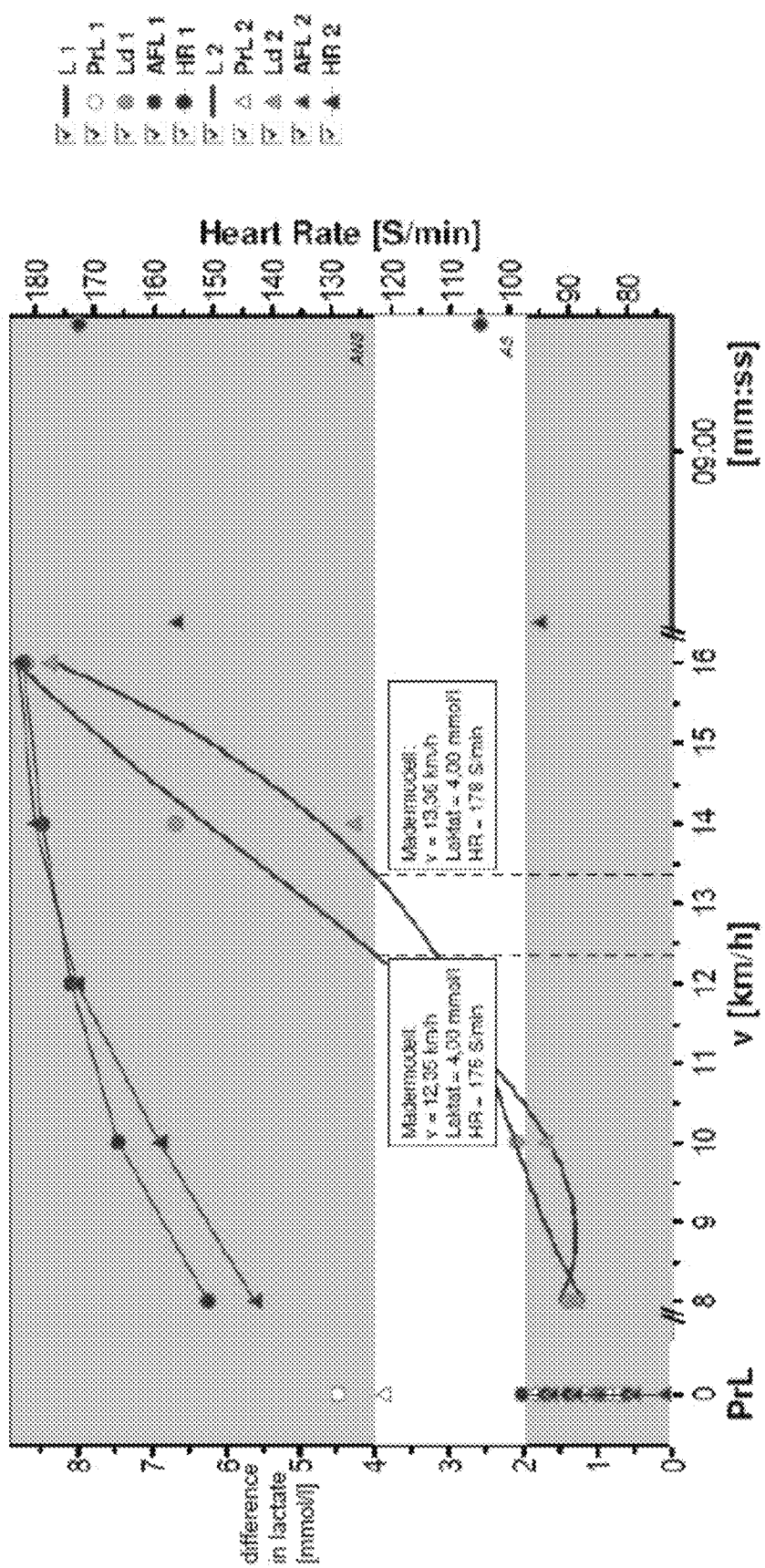
FIG. 7 shows a case study of the heart rate and lactate values of a respective individual proband with or without using the Thyroegym in the intervals in between two phases of physical strain (running)
Figure 8:
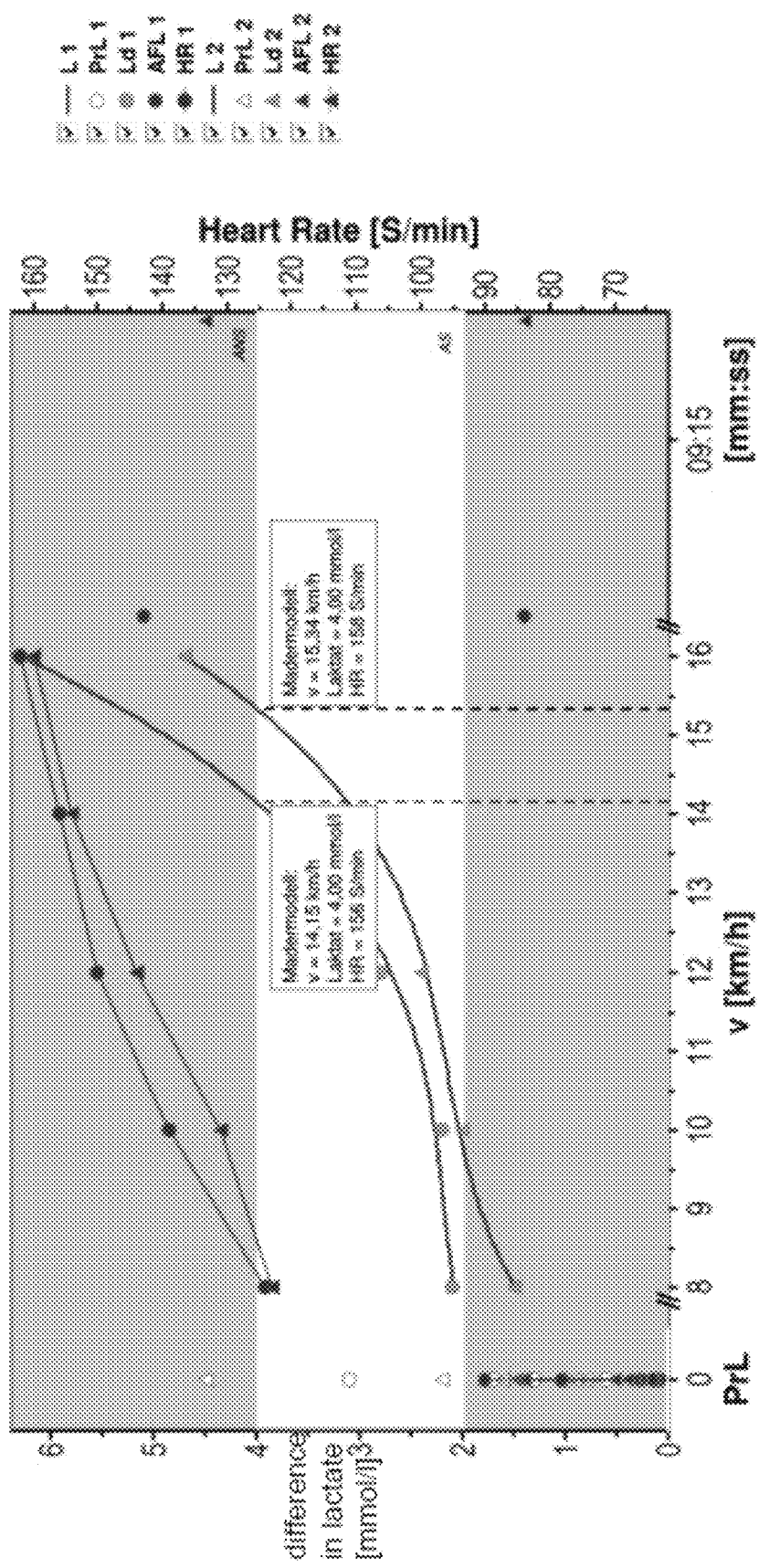
FIG. 8 shows a case study of the heart rate and lactate values of a respective individual proband with or without using the Thyroegym in the intervals in between two phases of physical strain (running).

These data show:
- improving the heart rate (pulse) to respiratory rate axis by applying the Thyreogym within breaks in between periods of physical strain: This leads to an economized heart rate and better cardiac function (run 1 without using the device Thyreogym: EDR=0.25 Hz; run 2 with application of the Thyreogym: EDR=0.23 Hz)
- less "consumption" in Entropy factor run 1 (Multiscale entropy=0.888-1.200 run 2 multiscale entropy=0.296-0.510) due to stimulation of the thyroid gland by the method of the invention Performance Profile Two case studies of individual probands give evidence in particular of the fact that the treatment according to the invention can result in a shift of the individual anaerobic threshold (FIGS. 7 and 8). The figures illustrate the heart rate and lactate values of a respective individual proband with or without using the Thyroegym in the intervals in between two phases of physical strain (running).

In the figures the anaerobic threshold of 4 mmol/l is depicted. It can be seen that the proband of FIG. 7 reached this threshold with a velocity of 13.36 km/h when he applying the Thyroegym. Without this treatment, the threshold had already been reached at 12.25 km/h. The proband of FIG. 8 reached the threshold at a velocity of 15.34 km/h under the treatment of the invention. Without the Thyreogym, already at 14.15 km/h the anaerobic threshold was reached.

Hence, these examples shows that the treatment of the invention results in a better performance of the subject before reaching the critical lactate value and entering the anaerobic metabolism. Increasing the performance until the anaerobic threshold is reached is also called "shift of the anaerobic threshold".

FURTHER REFERENCES

Tarvainen, Mika, P., Niskanen, Juha-P., et. al (2014): Kubios HRV—Heart rate variability analysis software. Computer Methods and Programs in Biomedicine 113; 210-220.

Hsu, C.-H., Tsai, M.-Y., Huang, G-S., et al (2012): Poincaré plot indexes of heart rate variability detect dynamic autonomic modulation during general anesthesia induction. Acta Anaesthesiologica Taiwanica 50; 12-18.

Hoyer, D. (2009): Zur Bedeutung und Analyse der Herzfrequenzvariabilitat. Das Neurophysiologie-Labor; 31, 3: 158-171.

German-Sallo Zoltan et al, (2015): Non-LinearMethods in HRV Analysis; ScienceDirect, Procedia Technology 22 (2016) 645-651.

Goldstein D S et al. L F power of heart rate variability is not a measure of cardiac sympathetic tone but may be a measure of modulation of cardiac autonomic outflows by baroreflexes; Exp Physiol. 2011 Dec.; 96 (12): 1255-1261.

Heart rate variability: standards of measurement, physiological interpretation and clinical use. Task Force of the European Society of Cardiology and the North American Society of Pacing and Electrophysiology. Circulation 1996; 93: 1043-1065.

Wittling W.: Diagnostik der Herzratenvariabilität: Einblicke in die autonom-nervöse Regulation von Stressverarbeitung, Befindlichkeit, Verhalten und Gesundheit. Trier, ZNF, 2009.

Bonen A. (1998): Lactate transporters (MCT proteins) in heart and skeletal muscles. Medicine & Science in Sports & Exercise 0195-9131/00/3204-0778/0.

Boutellier, U. (2006): Die Milchsäure. Schweizerische Zeitschrift für "Sportmedizin und Sporttraumatologie" 54 (3), 109-109.

Brooks, G A, Brooks, T G, Brooks S. (2008): Laktat als metabolisches Signal der Genexpression. Deutsche Zeitschrift für Sportmedizin 59 (12) 280-286.

Juel, C. (2004): Laktattransport im Skelettmuskel: Trainingsinduzierte Anpas sung und Bedeutung bei korperlicher Belastung. Deutsche Zeitschrift für Sportmedizin 55 (6), 157-160.

Leyendecker, N. (2008): Der Einfluss von Laktat auf die Signaltransduktion in mikrovaskulären Endothezellen.

Maassen, N., Bröning D. (2008): Physiologische "Nebenwirkungen" der Milchsäure. Dtsch. Z. Sportmed. 59: 292-296.

Pilegaard, H., Domino, K., Noland, T., Juel, C., Hellstein, Y., Halestrap, A. P., Bangsbo, J. (1999): Effect of high intensity exercise training on lactate/H+ transport capacity in human skeletal muscle. J Appl Physiol E255-E261.

Stegmann, H., Kindermann, W., Schnabel, A. (1981): Lactate kinetics and individual anaerobic threshold. Int J Sports Med 2: 160-165.

Wachter, Eva (2009): HRV-Schwellenbestimmung anhand Fahrradergometrie und Laufband im Verhältnis zu anaeroben Schwellen und Laktatschwellen. Berlin, Medizinische Fakultät Charité—Universitätsmedizin Berlin, Berlin. Online verfügbar unter http://nbn-resolving.de/urn:nbn:de:kobv:188-fudissthesis000000014069-8.

Weineck, Jurgen (2010): Optimales Training. Leistungsphysiologische Trainingslehre unter besonderer Berücksichtigung des Kinder- und Jugendtrainings: Spitta-Verlag.

Wittling, Werner; Wittling, Ralf Arne (2012): Herzschlagvariabilitat: Frühwarnsystem, Stress- und Fitnessindikator. Heiligenstadt: Eichsfeld-Verlag.

Wahl, P., Bloch, W., Mester, J. (2009): Moderne Betrachtungsweisen des Laktats: Laktat ein überschätztes und zugleich unterschätztes Molekül. Schweizerische Zeitschrift für "Sportmedizin und Sporttraumatologie" 57 (3), 100-107.

Wang, Y., Tonouchi, M., Miskovic, D., Hatta, H., Bonen, A. (2003): T3 increases lactate transport and the expression of MCT4, but not MCT1, in rat skeletal muscle. Am J Physiol Endocrinol Metab 285:E622-E628.

Rohracher H.: Standige Muskelaktivität (>>Mikrovibration<<), "Tonus und Konstanz der Korpertemperatur", Wien: Schriftenreihe Univ., 1959.

Rohracher H.: Permanente rhythmische Mikrobewegungen des Warmblüter Organismus (>>Mikrovibration<<), Die Naturwissenschaften 7, 49 Jg., 1962

Gallasch E., Kenner T.: Characterisation of arm microvibration recorded on an accelerometer; in Eur. J. Appl. Physiol. 75: 226-232, 1997

The invention claimed is:

1. A method of lowering the blood lactate concentration of an athlete, wherein said method comprises:
    applying a pulsating magnetic field to the thyroid area of an athlete in need thereof; and
    measuring the blood lactate concentration of said athlete following the application of said pulsating magnetic field.

2. The method according to claim 1, wherein the magnetic field has a field strength in the range of 0.1 to 100 µT.

3. The method of claim 1, wherein the pulsating magnetic field has a single frequency selected from the range of 1 to 100 Hz.

4. The method according to claim 1, wherein the athlete has a blood lactate level of at least 1.5 mmol/l.

5. The method according to claim 1, wherein the pulsating magnetic field is applied at least once daily.

6. The method according to claim 5, wherein the pulsating magnetic field is applied for a duration of 1 to 60 min.

7. The method according to claim 1, wherein the pulsating magnetic field is applied to the athlete directly after the termination of physical strain.

8. A method for treating hyperlactatemia or lactic acidosis, comprising:
    administering a pulsating magnetic field to the thyroid area of a subject with hyperlactatemia or lactic acidosis; and
    measuring the blood lactate concentration of said subject following the application of said pulsating magnetic field.

9. The method according to claim 8, wherein the subject has a resting blood lactate concentration of greater than 1.5 mmol/l.

10. The method according to claim 8, wherein the subject has a resting blood lactate concentration of greater than 3 mmol/l.

11. The method according to claim 8, wherein the subject has a resting blood lactate concentration of greater than 5 mmol/l.

* * * * *